US008039025B1

(12) United States Patent  (10) Patent No.: US 8,039,025 B1
Zaid et al.  (45) Date of Patent: *Oct. 18, 2011

(54) METHODS AND DOSAGE FORMS FOR THE TREATMENT OF HUMAN CANCERS

(75) Inventors: Gene H. Zaid, Sterling, KS (US); Thomas W. Burgoyne, Wichita, KS (US); Beth Ann Wolf, Hutchison, KS (US)

(73) Assignee: Life Plus, LLC, Sterling, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/157,249

(22) Filed: Jun. 9, 2011

Related U.S. Application Data

(63) Continuation of application No. 12/905,847, filed on Oct. 15, 2010.

(51) Int. Cl.
*A61K 36/00* (2006.01)
(52) U.S. Cl. ..................................... 424/725
(58) Field of Classification Search .................. None
See application file for complete search history.

(56) References Cited

U.S. PATENT DOCUMENTS

| | | | |
|---|---|---|---|
| 3,332,969 | A | 7/1967 | Hutt, Jr. et al. |
| 5,002,767 | A | 3/1991 | Massë |
| 5,118,671 | A | 6/1992 | Bombardelli et al. |
| 5,486,510 | A | 1/1996 | Bouic et al. |
| 6,030,622 | A | 2/2000 | Shehadeh |
| 6,139,897 | A | 10/2000 | Goto et al. |
| 6,413,571 | B1 | 7/2002 | Liu |
| 6,491,952 | B1 | 12/2002 | Sjoberg |
| 7,351,739 | B2 | 4/2008 | Ho et al. |
| 2006/0034944 | A1 | 2/2006 | Rushlow et al. |
| 2006/0104940 | A1 | 5/2006 | Heinrichs et al. |
| 2007/0142652 | A1 | 6/2007 | Arumughan et al. |
| 2007/0183993 | A1 | 8/2007 | Binder et al. |
| 2008/0102111 | A1 | 5/2008 | Imanaka |
| 2008/0221221 | A1 | 9/2008 | Zhou et al. |
| 2009/0304827 | A1 | 12/2009 | Kim |
| 2011/0098362 | A9* | 4/2011 | Zhou et al. ............ 514/699 |

FOREIGN PATENT DOCUMENTS

| | | |
|---|---|---|
| AU | 5213586 A | 9/1987 |
| CN | 1724555 | 1/2006 |
| EP | 0985411 | 3/2000 |
| KR | 2009029015 | * 3/2009 |
| WO | WO 0064921 | 11/2000 |
| WO | WO 02079219 | 10/2002 |
| WO | WO 2007/073583 | * 7/2007 |

OTHER PUBLICATIONS

Xu et al. Zhongguo Zhong Yao Za Zhi. Apr. 2009. vol. 34, No. 8, pp. 990-993.*
Awad, A. B. et al. "β-Sitosterol Activates Fas Signaling in Human Breast Cancer Cells." Phytomedicine 14 (2007) 747-754.
Baskar, Albert A. et al. "Chemopreventive Potential of β-Sitosterol in Experimental Colon Cancer Model—an in vitro and in vivo Study." BMC Complementary and Alternative Medicine 10:24 (2010) 1-10. Available online at http://www.biomedcentral.com/1472-6882/10/24.
El-Desouky, S. K. et al. "Piperazirum, a Novel Bioactive Alkaloid from *Arum palaestinum* Boiss." Tetrahedron Letters 48 (2007) 4015-4017. Available online at www.sciencedirect.com.
Said, O. et al. "Ethnopharmacological Aurvey of Medicinal Herbs in Israel, the Golen Heights and the West Bank Region." Journal of Ethnopharmacology 83 (2002) 251-265.
Ali-Shtayeh, Mohammed S. Et al. "Traditional Knowledge of Wild Edible Plants Used in Palestine (Northern West Bank): A Comparative Study." Journal of Ethnobiology and Ethnomedicine 4.13 (2008). Available online at http://www.ethnobiomed.com/content/4/1/13.
Anwar, Farooq et al. "Fatty Acid, Tocopherol and Sterol Compositions of Canadian Prairie Fruit Seed Lipids." J Am Oil Chem Soc 85 (2008): 953-959. First page only.
Awad, A. B. et al. "Beta-Sitosterol Enhances Tamoxifen Effectiveness on Breast Cancer Cells by Affecting Ceramide Metabolism." Mol Nutr Food Res 52(4) (2008): 419-26. Abstract only.
Awad, A. B. et al. "Beta-Sitosterol Inhibits Ht-29 Human Colon Cancer Cell Growth and Alters Membrane Lipids." Anticancer Res. 16(5A) (1996): 2797-804. Abstract only.
Awad, A. B. et al. "Inhibition of Growth and Stimulation of Apoptosis by Beta-Sitosterol Treatment of MDA-MB-231 Human Breast Cancer Cells in Culture." Int.J.Mol.Med. 5(5) (2000): 541-545. (Abstract only).
Awad, Atif B. Et al. "Phytosterols as Anticancer Dietary Components: Evidence and Mechanism of Action." Journal of Nutrition 130 (2000): 2127-2130. Downloaded from jn.nutrition.org on Jan. 7, 2010.
Behrman, E.J. et al. "Cholesterol and Plants." Journal of Chemical Education. Unknown volume and year. www.JCE.DivCHED.org, 2011.
Berges, R. R. et al. "Randomised, Placebo-Controlled Double-Blind Clinical Trial of β-Sitosterol in Patients with Benign Prostatic Hyperplasia." The Lancet 345 (Jun. 17, 1995): 1529-1532.
Berry, C.P. et al. "Analysis of Free and Esterified Sterols in Wheat Flour and Semolina." 534d Annual Meeting, Cooperative Investigation between North Dakota Agricultural Experiment Station and Crops Research Division (Nov. 1968): 616-626.
Bradford, P.G. et al. "Phytosterols as Anticancer Compounds." Mol Nutr Food Res. 51(2) (2007): 161-70. Abstract only.
Committee on Comparative Toxicity of Naturally Occurring Carcinogens, National Research Council. "Carcinogens and Anticarcinogens in the Human Diet: A Comparison of Naturally Occurring and Synthetic Substances." 1996. Abstract only. Available online at http://www.nap.edu/catalog.php?record_id=5150.
Das, U. N. "Gamma-linolenic Acid, Arachidonic Acid, and Eicosapentaenoic Acid as Potential Anticancer Drugs." Nutrition 6(6) (1990): 429-34. Abstract only.

(Continued)

*Primary Examiner* — Christopher R. Tate
(74) *Attorney, Agent, or Firm* — Hovey Williams LLP

(57) ABSTRACT

Methods for the treatment of human cancers, daily dosage forms for cancer patients, and methods of formulating the dosage forms are provided wherein the daily dosage form contains from about 10-6,000 mg of each of β-sitosterol, isovanillin, and linolenic acid. Preferably, the dosage forms are formulated by first creating an aqueous decoction of *Arum palaestinum* Boiss, followed by fortification of the decoction with additional quantities of β-sitosterol, isovanillin, and linolenic acid.

7 Claims, No Drawings

OTHER PUBLICATIONS

Das, U. N. et al. "Local Application of Gamma-linolenic Acid in the Treatment of Human Gliomas." Cancer Lett. 94(2) (1995): 147-55. Abstract only.

El-Desouky, S. K. et al. "A New Pyrrole Alkaloid Isolated from *Arum palaestinum* Boiss. And its Biological Activities." Arch.Pharm.Res. 30.8 (2007): 927-931.

Jacam Chemicals, LLC (sponsor). "Acute Oral Toxicity Up and Down Procedure in Rats." Eurofins Product Safety Laboratories, Study No. 24321. Apr. 14, 2008.

Jaradat, Dr. Nidal A. "Medical Plants Utilized in Palestinian Folk Medicine for Treatment of Diabetes Mellitus and Cardiac Diseases." J. Al-Aqsa Unv. 9 (2005): 1-28.

Jiang, W.G. et al. Inhibition of Hepatocyte Growth Factor—Induced Motility and In vitro Invasion of Human Colon Cancer Cells by Gamma-Linolenic Acid. British Jounral of Cancer 71(1995): 744-752.

Jiang, Wen G. et al. "Regulation of the Expression fo E-Cadherin on Human Cancer Cells by γ-Linolenic Acid (GLA)." Cancer Research 55 (Nov. 1, 1995): 5043-5048.

Kapetanovic, Radomir et al. "Sterol Composition of the Adriatic Sea Algae *Ultra lactuca, Codium dichotomum, Cystoseira adriatica and Fucus virsoides*.." J.SerbChem.Soc. 70 (12) (2005): 1395-1400.

Kuo, Reen-Yen et al. "Chemical Constituents and Their Pharmacological Activities from Formosan Annonaceous Plants." The Chinese Pharmaceutical Journal 54 (2002): 155-173.

Kuksis, A. et al. "Composition of Molecular Distillates of Corn Oil: Isolation and Identification of Sterol Esters." J. Lipid Research. 1 (1960): 311-320.

Peters, Wilbert H.M. et al. "Chapter 31—Antigenotoxins and Cancer." The Cancer Handbook. Ed. Lynn MacTaggart. Bloomingdale, IL: Vital Health Publishing, 1997. 421-434.

Saad, Bashar et al. "Tradition and Perspectives of Arab Herbal Medicine: A Review." eCAM (2005): 1-5. Downloaded from http://ecam.oxfordjournals.org on Mar. 15, 2010.

Shukla, R. S. et al. "Steroidal Composition of the Root Extract of *Orthosiphon tomentosus*, Benth (Lamiaceae) Used in Tribal Medicine." Journal of Pharmacy Research 2 (2009): 1137-1138.

Strum, Stephen B. "Beta-Sitosterol and the Aging Prostate Gland." LE Magazine (Jun. 2005). Available online at http://www.lef.org.

Sugimura, Takashi et al. "Chapter 28—Dietary Genotoxins and Cancer." The Cancer Handbook. Ed. Lynn MacTaggart. Bloomingdale, IL: Vital Health Publishing, 1997. 389-397.

Yan, Yu-Qian. "Vanillin Derivative 6-bromine-5-hydroxy-4-methozybenzaldehyde-Elicited Apoptosis and G2M Arrest of Jurkat Cells Proceeds Concurrently with DNA-PKcs Cleavage and Akt Inactivation." International Jounral of Oncology 29 (2006): 1167-1172.

Vachalkova, A. et al. "Taraxasterol and β-Sitosterol: New Naturally Compounds with Chemoprotective/chemopreventive Effects." Neoplasma 51 (2004): 407-14. Abstract only.

* cited by examiner

METHODS AND DOSAGE FORMS FOR THE TREATMENT OF HUMAN CANCERS

CROSS-REFERENCE TO RELATED APPLICATION

This is a continuation of identically-titled U.S. patent application Ser. No. 12/905,847, filed Oct. 15, 2010, which is incorporated herein by reference in its entirety.

BACKGROUND OF THE INVENTION

1. Field of the Invention

The present invention is directed to methods for the treatment of human cancers, daily dosage forms for administration to cancer patients, and methods of formulating such dosage forms. More particularly, the invention is concerned with the administration of daily dosage forms (e.g., aqueous mixtures, capsules, pills, or tablets) containing from about 10-6,000 mg of each of β-sitosterol, isovanillin, and linolenic acid. Such treatment provides a marked decline and/or elimination of cancerous tumors, particularly those of the bladder, breast, liver, and lung, and a corresponding enhancement of the wellness and lifestyles of the treated patients.

2. Description of the Prior Art

Cancer is a generic term for a large group of diseases that can affect any part of the body. Other terms used are malignant tumours and neoplasms. One defining feature of cancer is the rapid creation of abnormal cells that grow beyond their usual boundaries, and which can then invade adjoining parts of the body and spread to other organs. This process is referred to as metastasis. Metastases are the major cause of death from cancer.

Cancer is a leading cause of death worldwide. The disease accounted for 7.4 million deaths (or around 13% of all deaths worldwide) in 2004. The main types of cancer leading to overall cancer mortality each year are:

lung (1.3 million deaths/year)
stomach (803 000 deaths)
colorectal (639 000 deaths)
liver (610 000 deaths)
breast (519 000 deaths).

More than 70% of all cancer deaths occurred in low- and middle-income countries. Deaths from cancer worldwide are projected to continue rising, with an estimated 12 million deaths in 2030.

The most frequent types of cancer worldwide (in order of the number of global deaths) are:

Among men—lung, stomach, liver, colorectal, oesophagus and prostate
Among women—breast, lung, stomach, colorectal and cervical.

Cancer arises from one single cell. The transformation from a normal cell into a tumour cell is a multistage process, typically a progression from a pre-cancerous lesion to malignant tumours. These changes are the result of the interaction between a person's genetic factors and three categories of external agents, including:

physical carcinogens, such as ultraviolet and ionizing radiation
chemical carcinogens, such as asbestos, components of tobacco smoke, aflatoxin (a food contaminant) and arsenic (a drinking water contaminant)
biological carcinogens, such as infections from certain viruses, bacteria or parasites.

Some examples of infections associated with certain cancers:

Viruses: hepatitis B and liver cancer, Human Papilloma Virus (HPV) and cervical cancer, and human immunodeficiency virus (HIV) and Kaposi sarcoma.
Bacteria: *Helicobacter pylori* and stomach cancer.
Parasites: schistosomiasis and bladder cancer.

Aging is another fundamental factor for the development of cancer. The incidence of cancer rises dramatically with age, most likely due to a buildup of risks for specific cancers that increase with age. The overall risk accumulation is combined with the tendency for cellular repair mechanisms to be less effective as a person grows older.

Tobacco use, alcohol use, low fruit and vegetable intake, and chronic infections from hepatitis B (HBV), hepatitis C virus (HCV) and some types of Human Papilloma Virus (HPV) are leading risk factors for cancer in low- and middle-income countries. Cervical cancer, which is caused by HPV, is a leading cause of cancer death among women in low-income countries. In high-income countries, tobacco use, alcohol use, and being overweight or obese are major risk factors for cancer.

The most common cancer treatment modalities are surgery, chemotherapy, and radiation treatments. All of these techniques have significant drawbacks in terms of side effects and patient discomfort. For example, chemotherapy may result in significant decreases in white blood cell count (neutropenia), red blood cell count (anemia), and platelet count (thrombocytopenia). This can result in pain, diarrhea, constipation, mouth sores, hair loss, nausea, and vomiting.

Biological therapy (sometimes called immunotherapy, biotherapy, or biological response modifier therapy) is a relatively new addition to the family of cancer treatments. Biological therapies use the body's immune system, either directly or indirectly, to fight cancer or to lessen the side effects that may be caused by some cancer treatments.

The immune system is a complex network of cells and organs that work together to defend the body against attacks by "foreign" or "non-self" invaders. This network is one of the body's main defenses against infection and disease. The immune system works against diseases, including cancer, in a variety of ways. For example, the immune system may recognize the difference between healthy cells and cancer cells in the body and works to eliminate cancerous cells. However, the immune system does not always recognize cancer cells as "foreign." Also, cancer may develop when the immune system breaks down or does not function adequately. Biological therapies are designed to repair, stimulate, or enhance the immune system's responses.

Some antibodies, cytokines, and other immune system substances can be produced in the laboratory for use in cancer treatment. These substances are often called biological response modifiers (BRMs). They alter the interaction between the body's immune defenses and cancer cells to boost, direct, or restore the body's ability to fight the disease. BRMs include interferons, interleukins, colony-stimulating factors, monoclonal antibodies, vaccines, gene therapy, and nonspecific immunomodulating agents.

Researchers continue to discover new BRMs, to learn more about how they function, and to develop ways to use them in cancer therapy. Biological therapies may be used to:

Stop, control, or suppress processes that permit cancer growth.
Make cancer cells more recognizable and, therefore, more susceptible to destruction by the immune system.
Boost the killing power of immune system cells, such as T cells, NK cells, and macrophages.

Alter the growth patterns of cancer cells to promote behavior like that of healthy cells.

Block or reverse the process that changes a normal cell or a precancerous cell into a cancerous cell.

Enhance the body's ability to repair or replace normal cells damaged or destroyed by other forms of cancer treatment, such as chemotherapy or radiation.

Prevent cancer cells from spreading to other parts of the body.

A variety of medicinal plants have also been employed in the treatment of human cancers. For example, plants from the hills and mountains of Israel, Palestine, and the Golan Heights have been used for many years for the treatment of many human diseases, including cancers. Among these are extracts of *Arum palaestinum* Boiss. See, for example, Said et al. *Ethnopharmacological Survey of Medicinal Herbs in Israel, the Golan Heights and the West Bank Region*. J. Ethnopharmacology. 83 (2002): 251-265.

The National Institutes of Health estimated that the total cost of cancer care in the United States in 2005 was $209.9 billion. Direct medical costs including inpatient and outpatient care, drugs, and devices accounted for $74 billion of this total, $17.5 billion was attributed to indirect morbidity costs (ie, lost productivity), and indirect mortality costs (i.e, lost productivity due to premature death) accounted for $118.4 billion. Given that cancer is largely a disease of older individuals, cancer expenditures will be of even greater concern in the future as the so-called baby boomer population swells the ranks of the US Medicare program from 42.5 million in 2005 to almost 70 million by 2030. As evidence of this demographic trend (and as evidence of unmet clinical need in oncology relative to other disease contexts), cancer recently surpassed heart disease as the number one killer of Americans younger than 85 years.

Despite the immense amount of worldwide research and efforts to stem the tide of cancer and its side effects, the disease in its many manifestations continues to be a huge problem. Therefore, any new cancer treatment having a curative affect and/or the ability to ameliorate cancer symptoms and improve the lifestyle of patients is highly significant and important.

SUMMARY OF THE INVENTION

The present invention provides an improved method for the treatment of a variety of human cancers, most especially female breast and lung cancers, by the administration to a cancer patient of a dosage form containing from about 10-6,000 mg (more preferably from about 1,000-4,000 mg, still more preferably from about 2,500-, 3500 mg, and most preferably about 3,000 mg) of each of (3-sitosterol, isovanillin, and linolenic acid. The administration is preferably carried out on a daily basis for a period of time of at least about 21 days, and more preferably until elimination of the patient's cancer, or at least the amelioration of the patient's cancer symptoms. The products of the invention can be in any dosage form, such as an aqueous dispersion, capsule, pill, and tablet. The most preferred dosage form is an aqueous dispersion.

In preferred practice, the dosage forms of the invention are prepared employing a decoction or tea using plant parts (preferably leaves and/or roots) of *Arum palaestinum* Boiss, or any other suitable plant parts of the genus *Arum*. However, such decoctions, standing alone, do not have the requisite amounts of β-sitosterol, isovanillin, and linolenic acid required in the invention. Accordingly, it is necessary to supplement or fortify the plant decoctions using amounts of β-sitosterol, isovanillin, and linolenic acid not derived from the plant decoctions. Advantageously, amounts of essentially pure β-sitosterol, isovanillin, and linolenic acid are added to the plant decoctions to achieve the foregoing amounts of these ingredients. The linolenic acid may be added in the acid form or as a salt (e.g., sodium or potassium salt).

If it is desired to administer an aqueous dispersion dosage form, the above-described fortified decoctions can be used directly without further additions or modifications. On the other hand, it is equally possible to provide solid dosage forms by the lypholization of the fortified decoctions to yield solid extracts. In any case, the goal of administration is to provide to the patient the above-noted milligram amounts of each of β-sitosterol, isovanillin, and linolenic acid on a daily basis.

DETAILED DESCRIPTION OF THE PREFERRED EMBODIMENT

In preferred forms, the invention involves the administration of a dosage form prepared using plant parts of *Arum palaestinum* Boiss, which grows naturally in the Middle East, and particularly in Palestine and adjoining regions. This plant is of the genus *Arum*, family Araceae, subfamily Aroideae, and tribe Areae, and has a Nomen No. of 4357. The name was verified on Nov. 5, 1985 by ARS Systematic Botanists. The species priority site is the Ornamental Plant Germplasm Center. The plant is also known by common names, including Black Calla and Solomon's-Lily.

Analysis of *Arum palaestinum* Boiss

A detailed examination designed to determine the identity of the chemical components of *Arum palaestinum* Boiss was undertaken using Gas Chromatography-Mass Spectroscopy (GC-MS). In particular, one gram of dried plant leaf was boiled in 100 ml of dichloromethane for approximately 30 minutes. After cooling, the liquid was filtered, followed by solvent evaporation under nitrogen to a final volume of 8 ml. This liquid extract was then analyzed using GC-MS. conducted at North Carolina State University. The instrument used was an Agilent Technologies 5975 GC-MS equipped with a DB-5 column. Sample volumes injected were typically 1 μL with spitless injection. The GC inlet was maintained at 300° C. with the initial oven temperature set at 60° C. Three minutes after injection, the oven temperature was increased at a rate of 5° per minute to a final temperature of 325° C., which was held for five minutes.

Background samples were collected and analyzed throughout the entire sample preparation procedure. Retention time comparison, EI mass spectrum interpretation, accurate mass analysis, and known standard comparisons were used in the qualitative analysis. Quantitation was accomplished by comparing the unknown concentrations to a set of standards of known concentrations. The following table sets forth the results of this study, wherein the relative amounts of chemical ingredients were normalized to the amount of hexadecanoic acid:

| GCMS RESULTS | | |
|---|---|---|
| Molecule | Formula | Relative Amount |
| hexadecanoic acid | C16H32O2 | 1 |
| linolenic acid | C18H30O2 | 0.48 |
| linoleic acid | C18H32O2 | 0.44 |
| oleamide | C18H35NO | 0.12 |

-continued

GCMS RESULTS

| Molecule | Formula | Relative Amount |
|---|---|---|
| 2-monopalmitin | C19H38O4 | 0.17 |
| phytol | C20H40O | 0.49 |
| campesterol | C28H48O | 0.79 |
| sitostenone | C29H48O | 0.085 |
| stigmasterol | C29H48O | 0.29 |
| isofucosterol | C29H48O | 0.13 |
| 5a-stigmastane-3,6-dione | C29H48O2 | 0.038 |
| beta-sitosterol | C29H50O | 1.9 |
| cycloartenol | C30H50O | 0.19 |
| dl-a-tocopherol | C29H50O2 | 0.050 |
| heneicosane | C21H44 | 0.028 |
| tricosane | C23H48 | 0.093 |
| pentacosane | C25H52 | 0.29 |
| heptacosane | C27H56 | 0.88 |
| nonacosane | C29H60 | 2.1 |
| hentriacontane | C31H64 | 0.39 |
| 5,5,8a-Trimethyl-3,5,6,7,8,8a-hexahydro-2H-chromene | C12H20O | 0.15 |
| 6-(3,3-Dimethyl-oxiran-2-ylidene)-5,5-dimethyl-hex-3-en-2-one | C12H18O2 | 0.029 |
| 2-butanone, 4(2,6,6-trimethyl -1,3 cyclohexadien -1 -yl) | C13H20O | 0.070 |
| 2-cyclohexen-1-one, 4-(3-hydroxy-1-butenyl)-3,5,5-trimethyl | C13H20O2 | 0.042 |
| 2-cyclohexen-1-one, 4-(3-hydroxybutyl)-3,5,5-trimethyl- | C13H22O2 | 0.12 |
| 6-(3-Hydroxy-but-1-enyl)-1,5,5-trimethyl-7-oxabicyclo[4.1.0]heptan-2-ol | C13H22O3 | 0.17 |
| 3-Buten-2-one, 4-(4-hydroxy-2,2,6-trimethyl-7-oxabicyclo[4.1.0]hept-1-yl)- | C13H20O3 | 0.05 |
| isovanillin | C8H8O3 | 0.012 |
| cinnamic acid | C9H8O2 | 0.018 |
| 2 methoxy 4 vinylphenol | C9H10O2 | 0.035 |
| 2-propenal, 3-(4-hydroxy-3-methoxyphenyl) | C10H10O3 | 0.063 |
| docosyl hexadecanate | C16H33O2-C22H44 | 0.081 |

Preparation of Fortified Aqueous Decoction of *Arum palaestinum* Boiss

In the preferred procedure, from about 12-18 grams (more preferably about 15 grams) each of *Arum palaestinum* Boiss comminuted leaves and roots were placed in a vessel containing about one gallon of water, along with fortifying amounts (from about 1-50 grams, more preferably from about 15-40 grams, and most preferably about 25 grams) of pure β-sitosterol, isovanillin, and linolenic acid obtained from Sigma-Aldrich of St. Louis, Mo. The β-sitosterol and isovanillin are in solid form, whereas the linolenic acid is a liquid. The mixture was then brought to a hard boil for approximately 10-15 minutes. Thereupon, the heat was reduced and the mixture was allowed to simmer for an additional approximately 10-15 minutes. The simmered mixture was then allowed to cool to ambient, either naturally or by placing the vessel in ice, to yield a yellowish liquid.

In the next step, the cooled and fortified mixture was filtered through a common household sieve to remove large solids. This results in an aqueous product which can be administered orally to a cancer patient. The preferred dosage is a total of 6 ounces per day, preferably with a regiment of 2 ounces, 3 times per day, with shaking or mixing of the liquid prior to ingestion. The shelf life of the product is 3-4 weeks.

If desired, the cooled and fortified mixture can be lypholized (freeze-dried) to obtain a dried extract. This extract may be then put in capsule form or may be tableted to provide solid dosage forms.

Case Histories of Cancer Patients

The following case histories exemplify actual uses of the fortified aqueous liquid dosage form of the invention, where each patient was dosed at a total of 6 ounces of the liquid per day.

1.)

Patient Age: 50

Gender: M

Cancer Type: Squamous cell carcinoma, with primary site at the base of the tongue History: First diagnosed with squamous cell carcinoma in June, year 1. Cancer had metastasized to a lymph node in the neck with no primary cite identified. Problematic node removed by surgery as will as a complete tonsillectomy performed followed by radiation. In August, year 3, cancerous tumor found under patient tongue. Underwent radical tongue resection with forearm flap followed by radiation and chemotherapy. Base of tongue was determined to be primary cite of cancer. May of year 4, cancer again discovered in lymph nodes in neck. This was followed by another neck dissection and radiation. In March of year 5, cancer found at base of tongue, right side of neck, jaw and floor of mouth. This was followed by still another radical tongue resection with forearm flap, with neck dissection. In July of year 5, the cancer had returned to back of throat and floor of mouth. It was determined that no further surgery or radiation could safely be performed. Patient exhibited loss of appetite, loss of weight, lack of energy and generalized depression.

Prognosis: Diagnosis was terminal. Chemotherapy was given to slow the growth of tumors. PEG (stomach feeding tube) installed to allow for ingestion of nutrients once tumor had grown to the point where swallowing was impossible.

GHZ Product

History: Patient began taking GHZ-17 product in August of year 5, in conjunction with chemotherapy. Last session of chemotherapy was December, year 5. Patient continued to drink botanical product through February, year 6.

Outcome: Patient immediately showed an increase in appetite, energy level and weight gain. General attitude improved and patient began to exercise and participate in social activities. Tumors began to shrink in size and swallowing was no longer a problem. In March of year 6, scans indicated no tumors in any area of patient including the mouth, tongue, throat or any other part of the body. Patient has returned to full time work.

In July of year 6, cancer returned to throat and arm. Patient has difficulty in swallowing once again. Patient is back on chemotherapy as well as the botanical product. Upon resuming the GHZ-17 product, swallowing improved. Energy level and general attitude remain high. By October, tumors had shrunk in size and swallowing back to normal. Patient had gained 10 pounds lost during interval when swallowing was difficult and will return to work in early November. Chemotherapy is complete and patient will continue with GHZ-17 in an effort to reduce incidence of recurring tumors.

In April of year 7, the cancer returned to the larynx which is not operable. Patient underwent chemo with serious side effects. Patient experienced loss of weight and depression. Patient continued with the elixir and discontinued chemo. Diagnosis was terminal and not expected to live 2 months.

In August of year 7, the patient is showing signs of improvement. The elixir again improved the energy level and general disposition. Patient is not able to work but has begun to socialize. Diagnosis is for several more months of life.

2.)
Patient Age: 50
Gender: F
Cancer Type: Renal Cell Carcinoma, Stage 3
History: Patient diagnosed with Stage 3 Renal Cell Carcinoma on May 12, year 1. Tumor was 12 cm. Kidney and surrounding tissue was removed May 18, year 1. A CT scan in mid-July indicated the cancer had spread to the liver and lungs. Patient started chemotherapy (Sunitinib). Patient began to experience considerable pain, weakness, shortness of breath and lack of appetite. Patient also exhibited considerable jaundice.
Prognosis: Terminal
GHZ Product
History: Patient started taking GHZ-17 product in late August of year 1. Within 3 weeks the level of pain subsided and jaundice was visibly improved. In late September, x-rays indicated that the lung tumor had shrunk by 30%. Liver enzymes have risen to almost normal levels. Breathing has improved to the point where patient is now walking, going out to eat and shopping. Full set of MRI scans due October 16, year 1. In November, patient overall health was considerably improved and patient refused new scans. Will continue with GHZ-17 administration. In fall of year 1, patient stopped all treatment, including GHZ-17. Patient was diagnosed with kidney tumors in January of year 2.

3.)
Patient Age: 71
Gender: F
Cancer Type: Adenocarcinoma
History: Patient first diagnosed with lung cancer in August of year 1. In October of year 1, patient received a wedge resection to remove a portion of the left lung. In November of year 1, patient had a right lower lobectomy to remove the portion of her right lung that contained the largest tumor. In January of year 3, tumor appeared in the left lobe of the lung as well as observed lymph node enlargement on the mediastinum. Patient underwent radiation treatment. In February of year 3, patient was given 6 months to live. A new mass was found in the left lung and other nodes began to increase in size. All conventional treatment was stopped.
Prognosis: Terminal
GHZ-17 Product
History: Patient began taking GHZ-17 in July of year 3 for a period of 9 months.
Outcome: During the 9 months of GHZ-17 ingestion, both the small and large masses in the lung progressively shrunk to the point of disappearance. It also eliminated metastatic lesions. No new lesions or tumors have appeared. No adverse side effects observed as with traditional chemotherapy. Patient remains cancer-free in year 5.

4.)
Patient Age: 60
Gender: M
Cancer Type: Bladder Cancer
History: Patient observed blood in urine in year 1992, which was treated surgically. In 2000, the cancer returned. It was again treated with surgery and a series of BCG treatments that involve injecting live tuberculosis bacteria into the bladder to force the immune system to attack the cancer cells. For the next 6 years, patient had surgery yearly to remove new cancer growths. It was recommended that the patient receive an additional 6 BCG treatments.
Prognosis: Continued surgical and/or BCG treatments for remainder of life or unless the cancer spread to other areas of the body.
GHZ-17 Product
History: Patient began treatment with GHZ-17 in November of year 1, after the yearly surgeries. Continued treatment for 1 month.
Outcome: Patient tumors disappeared and patient has remained cancer free. There have been no further surgery or chemical treatments since year 2.

5.)
Patient Age: 49
Gender: F
Cancer Type: Breast Cancer
History: Patient observed lump in breast in August of year 1. Refused chemotherapy.
Prognosis: Without treatment, progression of cancer is inevitable.
GHZ-17 Product
History: Patient began taking GHZ-17 in August of year 1.
Outcome: Tumor size immediately shrunk. Subsequent scans have indicated no tumor in either breast. Patient remains cancer free through year 2.

6.)
Patient Age: 76
Gender: M
Cancer Type: Lung
History: Patient was diagnosed with lung cancer—Stage 4 in January of year 1. Immediately started chemotherapy and radiation. Subsequent scans indicated that cancer had spread to spine. Patient was diagnosed as terminal and all treatment stopped in May of year 1. Hospice called.
Prognosis: Terminal
GHZ-17 Product
History: Patient began taking GHZ-17 in June of year 1.
Outcome: Tumor in right lung disappeared, as did tumors in spine/back area. Patient overall health improved and patient expressed an interest in going to family outings etc. As tumors were shrinking, chemotherapy was again started. Patient experienced severe side effects including pain, difficulty in breathing, and unable to walk or stand. Patient also experienced tremors in hands. Scans of hip and spine indicated no presence of tumors that would cause this amount of pain. Chemo treatment was stopped. Patient is still taking botanical product but unknown prognosis. Patient is bed-ridden and on oxygen although, scans do not indicate cancer as the causative agent. Patient died September, year 1. Cause of death unknown.

7.)
Patient Age: 57
Gender: F
Cancer Type: Lung Cancer
History: Patient was first diagnosed with lung cancer in October of year 1. The cancer had not metastasized. Patient received both chemotherapy and radiation treatments.
Prognosis: If cancer can be contained in lung, prognosis is good.
GHZ-17 Product
History: Patient began taking GHZ-17 immediately upon diagnosis in conjunction with conventional treatments.
Outcome: Scans in December year 1 indicated significant reduction in tumor size. Scans in February year 2 indicated tumor was eradicated. No new signs of new cancer growth in any part of the body. November, year 2 the lining in patient's lung show signs of internal damage due to heavy radiation treatments. Patient diagnosed with pneumonia and put on ventilator. Patient died mid-November, year 2 of double pneumonia.

8.)
Patient Age: 63
Cancer Type: Colon Cancer
History: Patient was first diagnosed with colon cancer in October year 1. In January year 2 patient had a colon resection followed by 6 months of fulfox chemotherapy. In October of year 2, the cancer had metastases to liver. The patient underwent lever resection in January of year 3 in which the right lobe of the liver was removed. This was followed with 6 months of fulfuri chemotherapy. Liver tumors resurfaced in November of year 3. Patient underwent RFI followed by 3 months of fulfuri chemotherapy. In April of year 4, the cancer had spread and patient underwent a right lobectomy. In September of year 4, the patient had multiple inoperable tumors in both lungs and lymph node involvement.
Prognosis: Terminal
GHZ-17 Product
History: Patient began taking GHZ-17 in September of year 4.
Outcome: Progress continues to be monitored.

9.)
Gender: F
Patient Age: 22
History: Diagnosed with Maxillary Sinus cancer, squamous cell type on May 7, year 1. Patient received mixed chemotherapy (docetaxil, cisplatin and 5FU) starting June 3, year 1. Patient's white cell count dropped to dangerously low levels and the 5 FU drug was dropped from the treatment regiment. The tumor continued to grow and caused severe pain. Eye was swollen to the size of a large egg and patient was hospitalized for pain management on July 12. IMRT radiation treatments in combination with chemo (cisplatin) were started on July 13 to try and contain the size of the tumor. The tumor continued to grow in size and the 5FU chemo treatment was added back into the chemo treatment along with cetuximab or aka erbitux. There was a reduction in the tumor size during the last series of chemo. Last chemo and radiation was received on August 28. On August 20 patient experienced swelling in her lymph nodes. Biopsy indicated these growths to be moderately differentiated carcinoma. Patient went to MD Anderson for further evaluation in late August where it was determined that the cancer had spread to the T7 location of her thoracic spine. Surgery was ruled out as an option for treatment. It was also discovered at MD Anderson that the original diagnosis was incorrect and the correct cancer type is Sino-Masal Undifferentiated Carcinoma. This diagnosis changed the cancer drug used to treat her cancer to carboplatim and etoiside, which was started on October 6, year 1.
Prognosis: Patient will continue to aggressively treat the disease with available chemotherapy drugs.
GHZ-17 Product
History: Patient began taking GHZ-17 in mid-August, year 1.
Outcome: Since starting GHZ-17, the tumor in her sinus has shrunk. Tumors in lymph nodes continue to grow. Her overall energy level and appetite has increased and overall pain has decreased. Patient will continue with GHZ-17 in combination with prescribed chemo/radiation therapy. In November, patient's pain was considerably lessened. Reasonable tolerance to new chemotherapy drugs. Cancer has spread to other areas in September of year 1. Patient died in October, year 1.

10.)
Gender: M
Patient Age: 16
History: Patient was diagnosed with Hodgkin's Lymphoma on January 4, in year 1. Started chemotherapy in mid-January. White cell count dropped to 0.2. Chemo resumed in March where white cell count again dropped to 1.1. In April, the patient was hospitalized due to an infected porta cath. Porta Cath was removed and replaced with a PICC line.
Prognosis: Favorable outcome expected with a combination of chemotherapy and radiation.
GHZ17 Product
History: Patient began to take GHZ17 in mid-January along with chemo treatments. White cell counts, which were depressed following chemo, quickly returned to normal ranges. Energy levels remained high and patient even participated in tennis workouts at school.
Outcome: Patient's chemo treatments were cut off as tumors PET scan indicated no trace of cancer in May of year 1. Patient expected to resume normal life.

11.)
Gender: F
Patient Age: unknown
History: Patient has history of skin cancer. Approximately 30 pre-cancerous spots appeared on skin Spots will have to be surgically removed if they progress to cancerous cells.
GHZ17 Product
History: Patient took pulp from elixir and placed on pre-cancerous spot with a band-aid each night for approximately 1 month
Outcome: Spots disappeared leaving only a small scar in their place.

12.)
Gender: M
Patient Age: 40
Cancer Type: Originally diagnosed with lymphoma but biopsy did not confirm presence of cancer cells.
History: Originally diagnosed with lymphoma in October of year 1, but biopsy did not validate the presence of cancer cells. No chemotherapy given. Condition worsened in July of year 2. Once again the biopsy did not confirm the presence of cancer cells.
Prognosis: Patient was diagnosed with severe liver disorder and told his condition would deteriorate until a liver transplant was needed. Also told that his muscle tone, energy level and general health would never return to normal.
GHZ Product
History: Patient began taking GHZ17 in November of year 1. By May of year 2, his liver function had returned to near normal. His appetite, energy level and muscle tone has returned to near normal and his doctor stated that he would no longer need a liver transplant.
Outcome: Patient has resumed normal life activities and overall health is excellent.

Synopsis

All patients taking GHZ-17 experienced an increase in appetite, weight gain and energy boost. Whether taken in combination with other conventional treatments or alone, all patients showed a marked decline and/or eradication of tumors including those in the bladder, breast, liver, and lung. In those patients who tracked liver enzymes pre- and post-GHZ-17 administration, liver enzyme levels showed a marked increase during administration of GHZ-17. No negative side effects of GHZ-17 were noted in any case, although some patients expressed a dislike of the taste of GHZ-17.

Although not wishing to be bound by any theory of operation, the inventors believe that the methods of the invention reduce and/or eliminate cancer and/or the symptoms thereof by augmenting or stimulating the patients' immune systems. In this sense, the invention is believed to be a form of biological therapy. As such, it is considered that the invention is applicable to virtually all cancers, such as the following: Acute Lymphoblastic Leukemia, Adult; Acute Lymphoblastic Leukemia, Childhood; Acute Myeloid Leukemia, Adult; Acute Myeloid Leukemia, Childhood; Adreno cortical Carcinoma; Adrenocortical Carcinoma, Childhood; Adolescents, Cancer in; AIDS-Related Cancers; AIDS-Related Lymphoma; Anal Cancer; Appendix Cancer; Astrocytomas, Childhood; Atypical Teratoid/Rhabdoid Tumor, Childhood, Central Nervous System; Basal Cell Carcinoma; Bile Duct Cancer, Extrahepatic; Bladder Cancer; Bladder Cancer, Childhood; Bone Cancer, Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Brain Tumor, Central Nervous System Embryonal Tumors, Childhood; Brain Tumor, Astrocytomas, Childhood; Brain Tumor, Craniopharyngioma, Childhood; Brain Tumor, Ependymoblastoma, Childhood; Brain Tumor, Ependymoma, Childhood; Brain Tumor, Medulloblastoma, Childhood; Brain Tumor, Medulloepithelioma, Childhood; Brain Tumor, Pineal Parenchymal Tumors of Intermediate Differentiation, Childhood; Brain Tumor, Supratentorial Primitive Neuro ectodermal Tumors and Pineoblastoma, Childhood; Brain and Spinal Cord Tumors, Childhood (Other); Breast Cancer; Breast Cancer and Pregnancy; Breast Cancer, Childhood; Breast Cancer, Male; Bronchial Tumors, Childhood; Burkitt Lymphoma; Carcinoid Tumor, Childhood; Carcinoid Tumor, Gastrointestinal; Carcinoma of Unknown Primary; Central Nervous System Atypical Teratoid/Rhabdoid Tumor, Childhood; Central Nervous System Embryonal Tumors, Childhood; Central Nervous System (CNS) Lymphoma, Primary; Cervical Cancer; Cervical Cancer, Childhood; Childhood Cancers; Chordoma, Childhood; Chronic Lymphocytic Leukemia; Chronic Myelogenous Leukemia; Chronic Myeloproliferative Disorders; Colon Cancer; Colorectal Cancer, Childhood; Craniopharyngioma, Childhood; Cutaneous T-Cell Lymphoma; Embryonal Tumors, Central Nervous System, Childhood; Endometrial Cancer; Ependymoblastoma, Childhood; Ependymoma, Childhood; Esophageal Cancer; Esophageal Cancer, Childhood; Esthesioneuroblastoma, Childhood; Ewing Sarcoma Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Gastrointestinal Stromal Tumor (GIST); Gastrointestinal Stromal Cell Tumor, Childhood; Germ Cell Tumor, Extracranial, Childhood; Germ Cell Tumor, Extragonadal; Germ Cell Tumor, Ovarian; Gestational Trophoblastic Tumor; Glioma, Adult; Glioma, Childhood Brain Stem; Hairy Cell Leukemia; Head and Neck Cancer; Heart Cancer, Childhood; Hepatocellular (Liver) Cancer, Adult (Primary); Hepatocellular (Liver) Cancer, Childhood (Primary); Histiocytosis, Langerhans Cell; Hodgkin Lymphoma, Adult; Hodgkin Lymphoma, Childhood; Hypopharyngeal Cancer; Intraocular Melanoma; Islet Cell Tumors (Endocrine Pancreas); Kaposi Sarcoma; Kidney (Renal Cell) Cancer; Kidney Cancer, Childhood; Langerhans Cell Histiocytosis; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin, Adult; Lymphoma, Hodgkin, Childhood; Lymphoma, Non-Hodgkin, Adult; Lymphoma, Non-Hodgkin, Childhood; Lymphoma, Primary Central Nervous System (CNS); Macroglobulinemia, Waldenström; Malignant Fibrous Histiocytoma of Bone and Osteosarcoma; Medulloblastoma, Childhood; Medulloepithelioma, Childhood; Melanoma; Melanoma, Intraocular (Eye); Merkel Cell Carcinoma; Mesothelioma, Adult Malignant; Mesothelioma, Childhood; Metastatic Squamous Neck Cancer with Occult Primary; Mouth Cancer; Multiple Endocrine Neoplasia Syndromes, Childhood; Multiple Myeloma/Plasma Cell Neoplasm; Mycosis Fungoides; Myelodysplastic Syndromes; Myelodysplastic/Myeloproliferative Neoplasms; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin Lymphoma, Adult; Non-Hodgkin Lymphoma, Childhood; Non-Small Cell Lung Cancer; Oral Cancer, Childhood; Oral Cavity Cancer, Lip and; Oropharyngeal Cancer; Osteosarcoma and Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell Tumors; Papillomatosis, Childhood; Paranasal Sinus and Nasal Cavity Cancer; Parathyroid Cancer; Penile Cancer; Pharyngeal Cancer; Pineal Parenchymal Tumors of Intermediate Differentiation, Childhood; Pineoblastoma and Supratentorial Primitive Neuroectodermal Tumors, Childhood; Pituitary Tumor; Plasma Cell Neoplasm/Multiple Myeloma; Pleuropulmonary Blastoma, Childhood; Pregnancy and Breast Cancer; Primary Central Nervous System (CNS) Lymphoma; Prostate Cancer; Rectal Cancer; Renal Cell (Kidney) Cancer; Renal Pelvis and Ureter, Transitional Cell Cancer; Respiratory Tract Cancer with Chromosome 15 Changes; Retinoblastoma; Rhabdomyosarcoma, Childhood; Salivary Gland Cancer; Salivary Gland Cancer, Childhood; Sarcoma, Ewing Sarcoma Family of Tumors; Sarcoma, Kaposi; Sarcoma, Soft Tissue, Adult; Sarcoma, Soft Tissue, Childhood; Sarcoma, Uterine; Sézary Syndrome; Skin Cancer (Nonmelanoma); Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Cell Carcinoma; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Testicular Cancer, Childhood; Throat Cancer; Thymoma and Thymic Carcinoma; Thymoma and Thymic Carcinoma, Childhood; Thyroid Cancer; Thyroid Cancer, Childhood; Transitional Cell Cancer of the Renal Pelvis and Ureter; Trophoblastic Tumor, Gestational; Unknown Primary Site, Carcinoma of, Adult; Unknown Primary Site, Cancer of, Childhood; Unusual Cancers of Childhood; Ureter and Renal Pelvis, Transitional Cell Cancer; Urethral Cancer; Uterine Cancer, Endometrial; Uterine Sarcoma; Vaginal Cancer; Vaginal Cancer, Childhood; Vulvar Cancer; Waldenström Macroglobulinemia; Wilms Tumor; Women's Cancers.

We claim:

1. A human cancer treatment comprising administering to a cancer patient a daily dosage form containing from about 1,000-4,000 mg of each of β-sitosterol, isovanillin, and linolenic acid, said treatment including the step of administering said dosage form on a daily basis to a cancer patient, wherein said daily dosage form is prepared by the steps of:
    creating an aqueous decoction of *Arum palaestinum* Boiss; and
    fortifying said decoction by adding thereto amounts of β-sitosterol, isovanillin, and linolenic acid not derived from said decoction such that total quantities of β-sitosterol, isovanillin, and linolenic acid are each from about 1,000-4,000 mg.

2. The treatment of claim 1, wherein the fortified aqueous decoction is lypholized and provided in the form of a capsule.

3. A method of preparing a daily dosage form for the treatment of human cancers comprising the steps of:
    creating an aqueous decoction of *Arum palaestinum* Boiss; and
    fortifying said decoction by adding thereto amounts of β-sitosterol, isovanillin, and linolenic acid not derived from said decoction such that total quantities of β-sitosterol, isovanillin, and linolenic acid are each from about 1,000-4,000 mg.

4. The method of claim 3, said dosage form containing from about 2,500-3,500 mg of each of β-sitosterol, isovanillin, and linolenic acid.

5. The method of claim 3, the decoction-creating step comprising the steps of:
    comminuting plant parts of *Arum palaestinum* Boiss;
    placing said comminuted plant parts in water to form a mixture;
    boiling the mixture for a period of time; and
    allowing the mixture to cool.

6. The method of claim 5, said plant parts comprising from about 12-18 grams of leaves and from about 12-18 grams of root, said mixture comprising said leaves and root in about one gallon of water, including the step of boiling said mixture for a period of from about 10-15 minutes.

7. The method of claim 3, including the step of lyophilizing said fortified decoction.

\* \* \* \* \*